(12) United States Patent
Das

(10) Patent No.: US 7,604,614 B2
(45) Date of Patent: Oct. 20, 2009

(54) TEST METHOD AND APPARATUS FOR VERIFICATION OF MEDICAL DEVICE FUNCTIONALITY

(75) Inventor: Stephen D. Das, The Woodlands, TX (US)

(73) Assignee: Infusion Systems, LLC, Valencia, CA (US)

( * ) Notice: Subject to any disclaimer, the term of this patent is extended or adjusted under 35 U.S.C. 154(b) by 238 days.

(21) Appl. No.: 11/222,161

(22) Filed: Sep. 8, 2005

(65) Prior Publication Data

US 2006/0122652 A1 Jun. 8, 2006

Related U.S. Application Data

(60) Provisional application No. 60/625,429, filed on Nov. 5, 2004.

(51) Int. Cl.
*A61M 5/00* (2006.01)
(52) U.S. Cl. .................. 604/111; 604/131; 604/151
(58) Field of Classification Search .............. 604/111, 604/131, 151, 891.1
See application file for complete search history.

(56) References Cited

U.S. PATENT DOCUMENTS

| | | | |
|---|---|---|---|
| 3,585,963 A | 6/1971 | Hiszpanski | |
| 3,722,537 A | 3/1973 | Gregerson et al. | |
| 4,274,285 A * | 6/1981 | Purgold | 73/863.31 |
| 4,384,470 A | 5/1983 | Fiore | |
| 4,423,732 A | 1/1984 | Tarjan et al. | |
| 4,588,085 A | 5/1986 | Sussman | |
| 4,605,007 A | 8/1986 | Heraly | |
| 4,721,123 A | 1/1988 | Cosentino et al. | |
| 4,830,005 A | 5/1989 | Woskow | |
| 5,237,991 A | 8/1993 | Baker, Jr. et al. | |
| 5,383,338 A | 1/1995 | Bowsky et al. | |
| 6,292,697 B1 | 9/2001 | Roberts | |
| 6,467,506 B1 | 10/2002 | Nguyen | |
| 6,554,798 B1 * | 4/2003 | Mann et al. | 604/131 |
| 2002/0113606 A1 | 8/2002 | Hansen et al. | |
| 2003/0047128 A1 | 3/2003 | Delp | |
| 2004/0106874 A1 * | 6/2004 | Eigler et al. | 600/486 |
| 2005/0273059 A1 * | 12/2005 | Mernoe et al. | 604/180 |

\* cited by examiner

*Primary Examiner*—Kevin C Sirmons
*Assistant Examiner*—Bhisma Mehta
(74) *Attorney, Agent, or Firm*—Henricks, Slavin & Holmes LLP

(57) ABSTRACT

This invention relates to methods, apparatuses and systems for testing the functionality of the pumping mechanism of a medical device, e.g., an implantable infusion pump, while the medical device is contained within a shipping package. The test apparatus enables such functional verification, without opening the shipping package, when the medical device is still contained within the package that has been appropriately sealed to maintain sterility of the medical device.

16 Claims, 4 Drawing Sheets

TEST METHOD AND APPARATUS FOR VERIFICATION OF MEDICAL DEVICE FUNCTIONALITY

RELATED APPLICATION

This application claims the benefit of U.S. Provisional Application 60/625,429 filed on 5 Nov. 2004 which is incorporated herein by reference.

FIELD OF THE INVENTION

This invention relates to a method and apparatus for testing the functionality of a medical device, e.g., an implantable infusion pump, while the device is still contained within a sterile shipping package.

BACKGROUND OF THE INVENTION

Applications exist which require that devices be kept in a sterile package prior to use. For example, it is generally understood in the medical community that contaminants or infectious material should not be introduced into the human body. To that end, medical devices, and particularly devices intended for implantation in the body, such as infusion pumps, are preferably assembled under sterile conditions and shipped in packages which are appropriately sealed to maintain the sterile environment. Such packages generally remain sealed until they are opened immediately prior to surgically implanting the device.

It is, of course, important to verify that the device is operable, i.e., functional, prior to implanting. To assure the availability of at least one functional device, it is common practice to supply multiple devices to the surgical location prior to implantation. This practice can be inconvenient, can introduce delays in surgery, and can increase costs.

SUMMARY OF THE INVENTION

The present invention is directed to a method and apparatus which enables the functionality of a medical device for discharging fluid, e.g., an implantable infusion pump, to be verified while the device is contained in a sterile package. More particularly, the invention is concerned with medical devices which include an actuatable fluid transfer mechanism, e.g., a pump and/or valve mechanism.

In accordance with the invention, the medical device will be placed in a package prior to shipment from its place of manufacture. The package is then appropriately sealed to establish a sterile environment for the device. Subsequently, and before opening the package to access and use the device, the device is actuated, e.g., by an RF command signal transmitted from outside of the package, and the response of the device is then monitored. An indication is then produced, recognizable by a responsible user, to indicate whether the device is functional, i.e., whether or not the monitored response satisfies some predetermined criteria.

In a preferred embodiment, the medical device comprises an implantable infusion pump. A simple low cost test apparatus is mounted on or coupled to an outlet port of the infusion pump prior to placing the pump into the package. The test apparatus is configured to detect pump activity (e.g. a fluid discharge and/or a pressure change at the outlet port) and provide an indication thereof, e.g., visual and/or aural, recognizable by a responsible person. Prior to opening the package, the infusion pump is actuated (while still in the package) by a command signal generated by a transmitter externally of the package and communicated to a receiver within the infusion pump.

A preferred test apparatus in accordance with the invention is coupled to an infusion pump's catheter outlet port and is configured to provide a visual indication in response to pump activity (i.e. fluid discharge and/or pressure change) at the outlet port. The indication is visible externally of the package through a transparent portion or window in the package. Thus, without opening the sterile package, a responsible person can determine whether the pump is functioning in response to the externally generated command signal.

A preferred test apparatus in accordance with the invention includes an elongate tube having its open proximal end coupled to the pump's outlet port. The tube contains a column of gas, e.g., air, and a sealed distal end. As liquid is discharged from the outlet port into the tube, the liquid moves the gas/liquid interface, which can be visually observed by the responsible person through the window in the package.

In alternative embodiments of the invention, a flexible membrane, or a piston, can be coupled to the pump outlet port in lieu of the elongate tube to exhibit physical movement in response to a fluid discharge and/or pressure change from the port. In a further alternative embodiment, the visual indication can comprise a light source which can be activated in response to detected pump activity.

In a yet further alternative embodiment of the invention, the test apparatus can be configured to produce an aural indication in response to detected pump activity. For example, a buzzer, bell, chime, etc., can be activated to provide a sound recognizable by the responsible person.

In a still further embodiment, the test apparatus can transmit a signal externally of the package to indicate detected pump activity.

DETAILED DESCRIPTION

Figure 1:
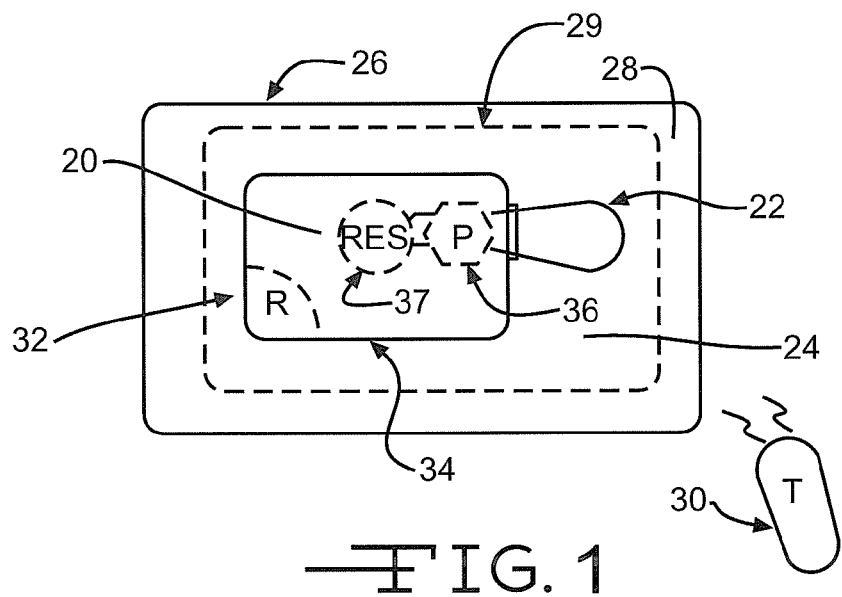
FIG. 1 is a block diagram of an exemplary implantable infusion pump, connected to a test apparatus in accordance with the invention, within a shipping package.

FIG. 1 illustrates an exemplary block diagram of a medical device, e.g., an implantable infusion pump 20, connected to a test apparatus 22 in accordance with the invention. The pump 20 and apparatus 22 are configured to be placed within an interior cavity 24 of a shipping package 26. A transparent cover 28 overlays and appropriately seals the cavity 24 at its boundary 29 to maintain a sterile environment within the shipping package 26. Once the infusion pump 20 and test apparatus 22 are sealed in the shipping package 26, the functionality of the infusion pump 20 can be verified by transmitting a command signal, e.g., RF, from an external transmitter 30 to a receiver 32 within the case 34 of the implantable infusion pump 20.

Typical implanted infusion pumps include a receiver and/or transceiver for receiving telemetry data and critical signals from an external transmitter and for transmitting patient and/or infusion pump condition data to an external (non-implanted) control unit or monitoring station. It is contemplated that such a receiver and/or transceiver be used as the receiver 32 in accordance with the present invention. In response to the command signal, the receiver 32 actuates a fluid transfer device 36, e.g., a pumping mechanism, within the case 34 to transfer fluid, e.g., liquid, from a reservoir 37 within the interior of the case 34 for discharge through the infusion pump's 20 outlet port, which is associated with the exterior of the case. The test apparatus 22 in accordance with the present invention functions to detect actuation of the mechanism 36, as by sensing whether a fluid discharge has occurred.

Figure 2:
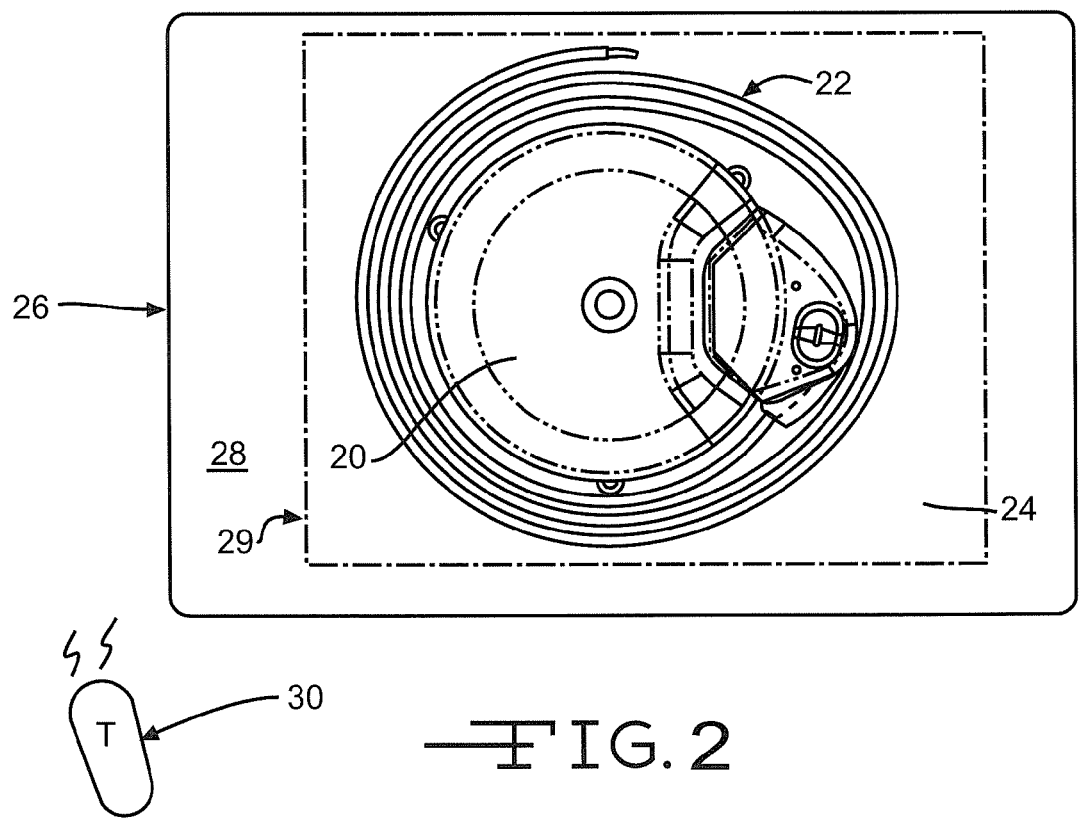
FIG. 2 is a plan view of an exemplary implantable infusion pump, connected to a test apparatus in accordance with the invention, within a shipping package.

FIG. 2 illustrates an exemplary implantable infusion pump 20 connected to a preferred test apparatus 22 in accordance with the invention. The infusion pump 20 and apparatus 22 are shown mounted in an exemplary sterile shipping package 26. The boundary seal 29 of the transparent cover 28 maintains the infusion pump 20 in a sterile environment preventing contamination unless the integrity of the transparent cover 24 or boundary seal 29 is compromised. The shipping package 26 schematically depicted in FIG. 2 is exemplary only but representative of various types of packaging which can be used with the test apparatus 22. Alternatively, the test apparatus 22 is suitable for use with any sealed bag or other container having a transparent area through which a visual indication produced by the test apparatus 22 can be viewed.

Figure 3:
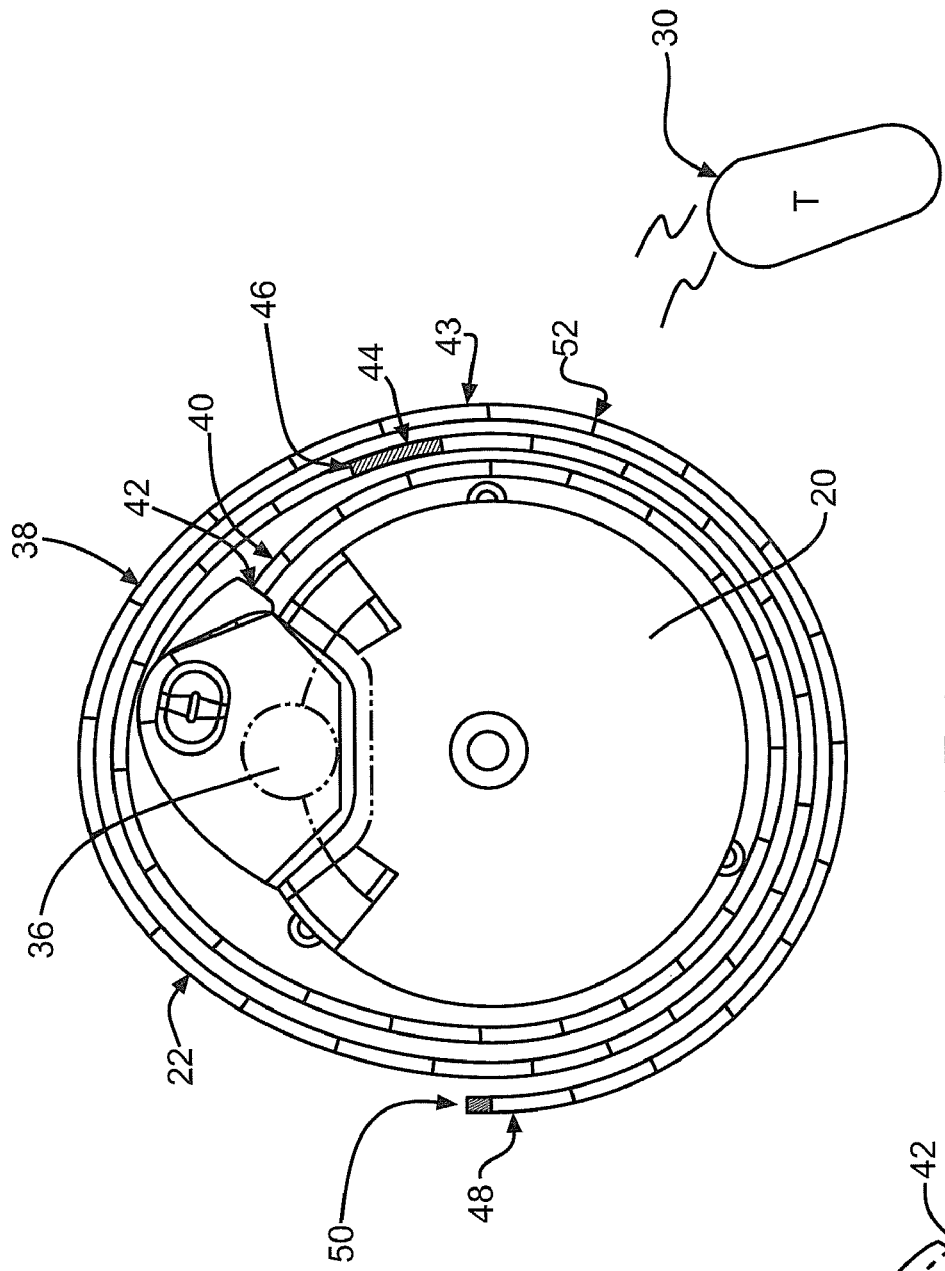
FIG. 3 is an enlarged plan view of the exemplary infusion pump of FIG. 2 (with the shipping package omitted) illustrating the test apparatus in greater detail.
Figure 3A:
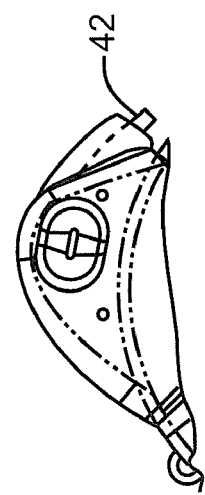
FIG. 3A shows a portion of the exemplary infusion pump with the test apparatus removed.

Attention is now directed to FIG. 3 which illustrates in greater detail a preferred embodiment of the test apparatus of FIG. 2. The test apparatus 22 comprises a transparent tube 38 having a proximal end 40 attached to the catheter outlet port 42 of the infusion pump 20. in other words, the proximal end 40 is a means that performs the function of mounting a device, i.e. the transparent tube 38, on a medical device outlet, i.e. the catheter outlet port 42. When the receiver 32 (FIG. 1) receives a command signal from the transmitter 30, it actuates the pumping mechanism 36 to define an operating state which transfers liquid from reservoir 37 (FIG. 1) for discharge through the catheter outlet port 42 into the transparent tube 38. The movement of liquid through the tube 38 is visible through the transparent cover 28 and provides a visual indication of functionality of the infusion pump 20 to a responsible observer.

In a preferred embodiment, the tube 38 is filled with sterile liquid 43, e.g., the same liquid used to fill the reservoir 37 (FIG. 1) prior to shipment. The liquid in the tube 38 preferably contains a short column of gas, e.g., air 44. After filling, the tube 38 is attached to the catheter outlet port 42 of the implantable infusion pump 20. When the pumping mechanism 36 is actuated in response to a command signal received by receiver 32 (FIG. 1), liquid discharged from the outlet port 42 will move the liquid/gas interface 46 inside the tube 38. The movement of the interface 46 can be readily observed through transparent cover 28, indicating proper operation of the implantable infusion pump 20.

In most applications, it is preferable to seal the distal end 48 of the tube 38 with a cap/plug 50, of a material such as silicone, to prevent evaporation or leakage of liquid. If the tube 38 is sealed with a cap/plug 50, the tube 38 can be marked with calibration or volume marks 52 to indicate the actual volume of liquid pumped into tube 38. If leakage or evaporation is not an issue and the need to measure fluid discharge is not required, the distal end 48 of the tube 38 need not be sealed, so long as the tube has sufficient capacity to accommodate the liquid discharge.

The tubing 38 is preferably coiled around the implantable infusion pump 20 such that its entire length is visible through the transparent cover 28 (not shown in FIG. 3). The specific dimensions of the tube 38 can vary dependent upon the size of the implantable infusion pump 20. It must, of course, be long enough to accommodate a volume of discharged liquid sufficient to verify pump functionality. An exemplary tube length could be approximately 22 inches or roughly three times the circumference of the exemplary infusion pump 20. An exemplary tube inner diameter could be about 0.047 inches, approximately equal to the diameter of a catheter for which the outlet port 42 is sized.

Figure 4:
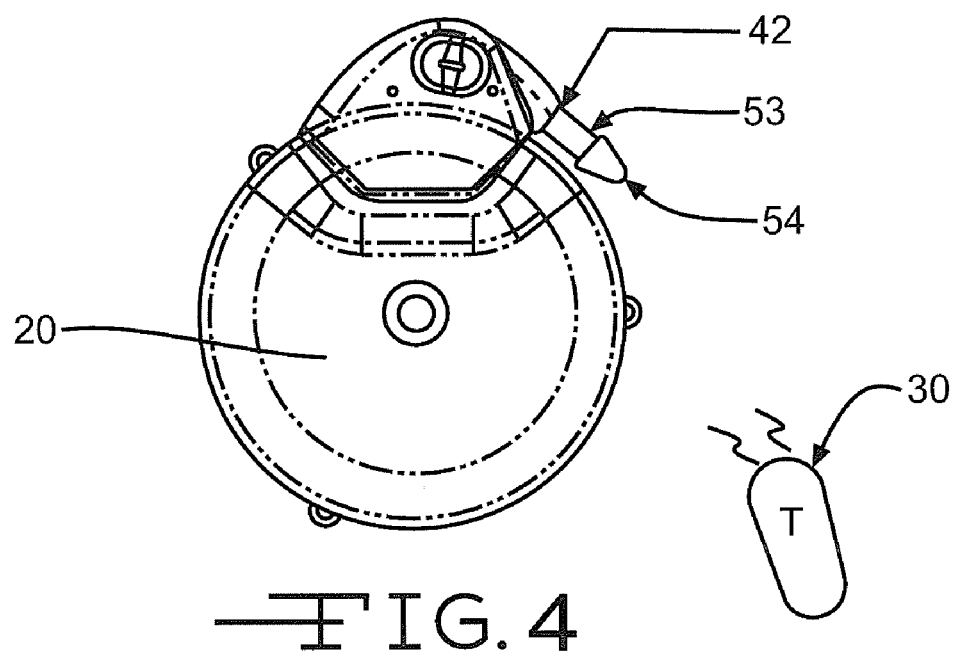
FIG. 4 is a plan view of an exemplary infusion pump connected to an alternative embodiment of the invention using a membrane.

Visual indications of pump activity can be produced in alternative ways. For example, FIG. 4 shows a short tube 53 coupling the outlet port 42 to a flexible membrane 54. in other words, the short tube 53 is a means that performs the function of mounting a device, i.e. the membrane 54, on a medical device outlet, i.e. the outlet port 42. When the pump is activated to pump liquid out of port 42, the liquid discharge will cause the membrane 54 to distend. This membrane distention can be visually observed through the transparent cover 28 to indicate pump functionality.

Figure 5:
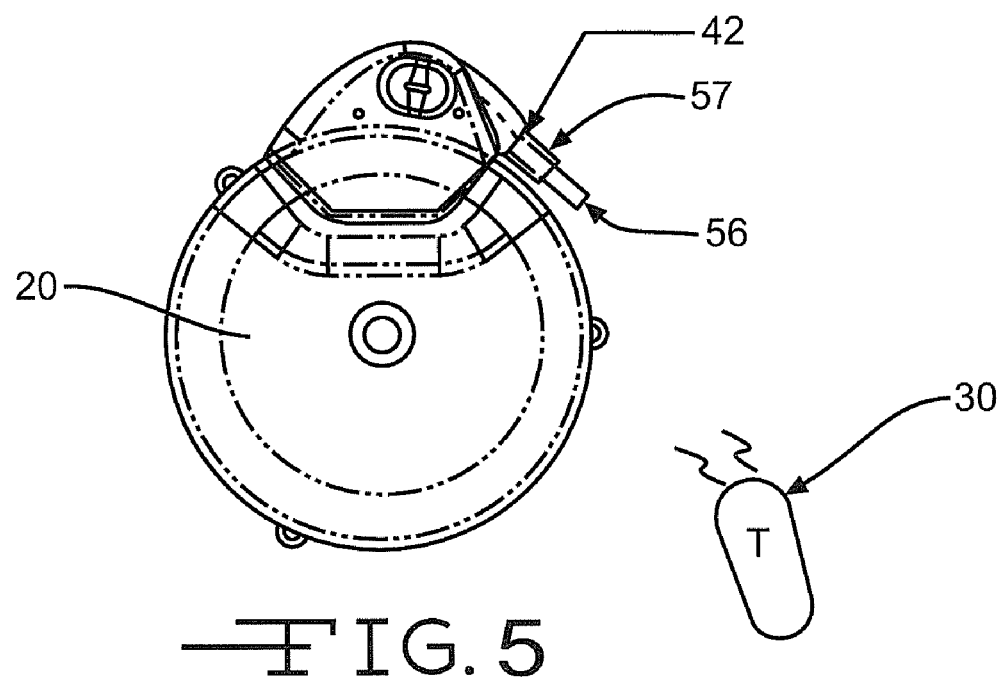
FIG. 5 is a plan view of an exemplary infusion pump connected to an alternative embodiment of the invention using a piston.

FIG. 5 illustrates another alternative visual indication embodiment in which a piston 56 is used in lieu of the membrane 54 of FIG. 4. In FIG. 5, the liquid discharge from port 42 will produce a pressure on piston 56 which acts on the piston 56 to slide it outwardly from supporting sleeve 57. Supporting sleeve 57 is a means that performs the function of mounting a device, i.e. the piston 56, on a medical device outlet, i.e. the outlet port 42.

Figure 6:
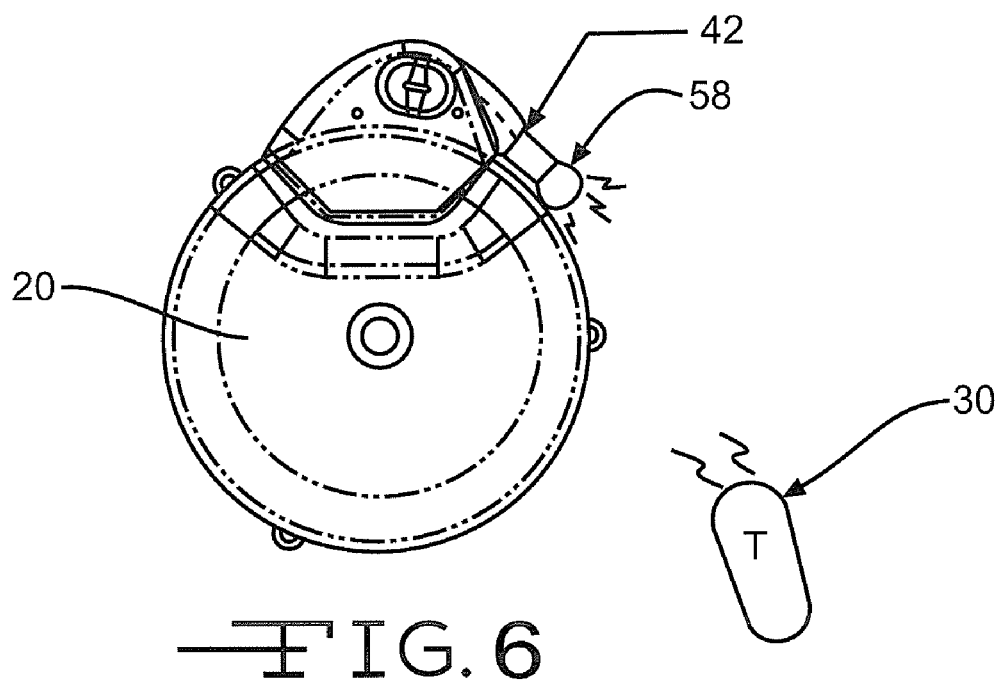
FIG. 6 is a plan view of an exemplary infusion pump connected to an alternative embodiment of the invention using a light source.

FIG. 6 illustrates a further alternative visual indication embodiment in which the liquid discharged from port 42 operates a switch (not shown) to activate a light source 58 which can be visually observed through the transparent cover 28 to indicate pump functionality. The tube, between the light source 58 and the outlet port 42, is a means that performs the function of mounting a device, i.e. the light source 58, on a medical device outlet, i.e. the outlet port 42.

Figure 7:
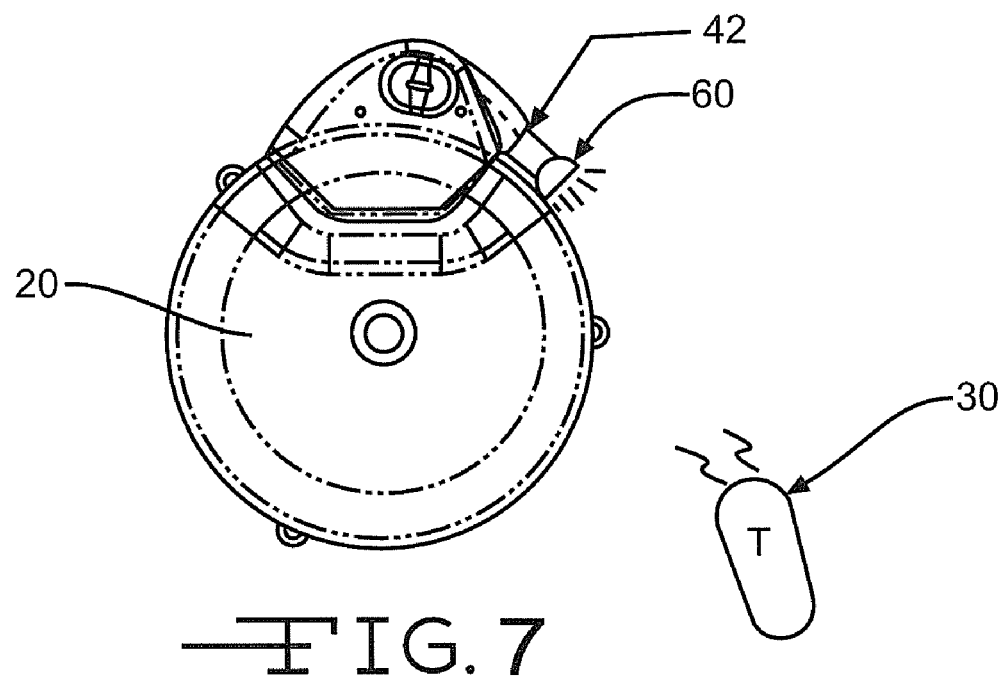
FIG. 7 is a plan view of an exemplary implantable infusion pump connected to a further alternative embodiment of the invention using a sound source.

FIG. 7 depicts a still further embodiment which utilizes a sound generator 60, e.g., a buzzer, chime, etc., for responding to liquid discharge from port 42 to produce an audible signal. The tube, between the sound generator 60 and the outlet port 42, is a means that performs the function of mounting a device, i.e. the sound generator 60, on a medical device outlet, i.e. the outlet port 42.

In a still further alternative embodiment, the sensing of pump activity after receipt of an externally transmitted command signal causes a transceiver internal to the infusion pump to transmit an indicating signal externally of the sterile package. This indicating signal can then be recognized by an external (non-implanted) control unit or other monitoring device to alert the responsible person.

From the foregoing, it should now be appreciated that an inexpensive test apparatus has been described for testing the functionality of an infusion pump while still contained in its sterile shipping package. Although only a limited number of embodiments have been illustrated, it is recognized that variations and modifications will occur to those skilled in the art coming within the spirit and scope of the invention as defined by the appended claims.

The invention claimed is:

1. A testing apparatus for use with a medical device that includes an outlet, is configured to produce a fluid discharge through the outlet and is contained in a sterile package, said testing apparatus comprising:
    an RF transmitter external to the sterile package for generating a command signal to the medical device;
    a receiver, which is part of the medical device, for responding to the command signal to actuate the medical device; and
    an indicator including a device within the sterile package configured to produce a user-discernible indication in response to fluid emission from the outlet and means for mounting the device on the medical device outlet.

2. The apparatus of claim 1 wherein the device comprises a light source.

3. The apparatus of claim 1 wherein the device comprises a sound source.

4. A testing apparatus for use with a medical device that includes an outlet, is configured to produce a fluid discharge through the outlet and is contained in a sterile package, said testing apparatus comprising:
    a transmitter external to the sterile package for generating a command signal to the medical device;
    a receiver, which is part of the medical device, for responding to the command signal to actuate the medical device; and
    an indicator within the sterile package including a tubing mounted to the medical device and having sufficient transparency to produce a user-discernible indication which enables a user to visually discern movement of fluid within the tubing in response to fluid emission from the outlet.

5. A system, comprising:
    an infusion pump that can be actuated to produce a fluid discharge from a pump outlet port;
    a sterile package for housing said infusion pump in a sterile environment;
    a transmitter external to said sterile package for selectively generating a command signal;
    a receiver mounted in said sterile package for responding to the command signal for switching said infusion pump to an operating state for producing fluid discharge; and
    a distendible membrane responsive to fluid pressure generated by the infusion pump at the pump outlet port.

6. A system, comprising:
    an infusion pump that can be actuated to produce a fluid discharge from a pump outlet port;
    a sterile package for housing said infusion pump in a sterile environment;
    a transmitter external to said sterile package for selectively generating a command signal;
    a receiver mounted in said sterile package for responding to the command signal for switching said infusion pump to an operating state for producing fluid discharge; and
    a visual tube having an open proximal end coupled to said pump outlet port for accommodating fluid discharged therefrom, wherein the visual tube has sufficient transparency to enable fluid movement within the tube to be observed outside of the tube.

7. The system of claim 6 wherein said transmitter comprises an RF transmitter.

8. The system of claim 6, further comprising:
    a liquid/gas interface movable within said visual tube, wherein the gas is placed between two liquid portions within said visual tube.

9. The system of claim 6 wherein said visual tube is marked with lines to indicate specific liquid volumes.

10. A method, comprising the steps of:
    providing an infusion pump having a case defining an interior and an exterior, a fluid transfer device and a reservoir within the interior, and an outlet port associated with the exterior;
    providing a sterile shipping package having a cavity therein;
    mounting said infusion pump in said cavity;
    sealing said cavity to contain a sterile environment therein;
    transmitting a pump actuation command signal to the infusion pump within the sterile shipping package from outside of said sterile shipping package; and
    providing an indication, which is discernible outside of said package, of any fluid discharge and/or pressure change which occurs at the outlet port in response to the pump actuation command signal.

11. The method of claim 10 wherein the indication comprises movement that is visually discernable outside of said sterile shipping package.

12. The method of claim 10 wherein the indication comprises light from a light source.

13. The method of claim 10 wherein the indication comprises sound from a sound source.

14. The method of claim 10 wherein said step of providing an indication further includes: sensing a fluid discharge and/or a pressure change at said outlet port.

15. A method, comprising the steps of:
    providing an infusion pump having an outlet port;
    providing a sterile shipping package having a cavity therein;
    mounting said infusion pump in said cavity;
    sealing said cavity to contain a sterile environment therein;
    transmitting a pump actuation command signal to the infusion pump within the sterile shipping package from outside of said sterile shipping package; and
    providing an indication, which is visually discernible outside of said package, of any fluid discharge and/or pressure change which occurs at the outlet port in response to the pump actuation command signal in the form of a movement of a membrane or a piston.

16. A testing apparatus for use with a medical device that includes an outlet, is configured to produce a fluid discharge through the outlet and is contained in a sterile package, said testing apparatus comprising:
    an RF transmitter external to the sterile package for generating a command signal to the medical device;
    a receiver, which is part of the medical device, for responding to the command signal to actuate the medical device; and
    an indicator mounted within the sterile package on the medical device outlet, selected from the group consisting of a distendible, flexible membrane that movably responds to fluid pressure and a slidable piston that movably responds to fluid pressure, and configured to produce a visible movement in response to fluid emission from the outlet.

* * * * *